(12) United States Patent
Ohshiro

(10) Patent No.: US 6,673,632 B1
(45) Date of Patent: *Jan. 6, 2004

(54) METHOD FOR MEASURING URINARY TRYPSIN INHIBITOR

(75) Inventor: Kyouichi Ohshiro, Kyoto (JP)

(73) Assignee: Kyoto Daiichi Kagaku Co., Ltd., Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,942

(22) Filed: Aug. 14, 1998

(30) Foreign Application Priority Data

Aug. 15, 1997 (JP) ............................................. 9-220495

(51) Int. Cl.⁷ .................... G01N 33/536; G01N 33/543; G01N 33/557; G01N 33/00
(52) U.S. Cl. .......................... 436/536; 422/73; 436/501; 436/517; 436/518
(58) Field of Search ............................ 422/73; 436/501, 436/517, 518, 536

(56) References Cited

U.S. PATENT DOCUMENTS

| | | | |
|---|---|---|---|
| 4,080,264 A | * 3/1978 | Cohen et al. | 195/103.5 |
| 4,148,869 A | 4/1979 | Deaton | |
| 4,174,952 A | * 11/1979 | Cannell et al. | 23/230 |
| 4,703,018 A | * 10/1987 | Craig et al. | 436/518 |
| 5,100,805 A | * 3/1992 | Ziege et al. | 436/517 |
| 5,175,112 A | * 12/1992 | Amiral et al. | 436/533 |
| 5,409,895 A | * 4/1995 | Morishita et al. | 514/12 |
| 5,891,664 A | * 4/1999 | Dan o et al. | 435/69.1 |

FOREIGN PATENT DOCUMENTS

| EP | 0 483 512 | 9/1991 |
|---|---|---|
| EP | 0 764 849 | 9/1996 |
| JP | 60-94404 | 5/1985 |
| JP | 4-198866 | 7/1992 |

OTHER PUBLICATIONS

Maehara et al. 1985. Immunochemical Determination of the Serum Protein Reacting with Antibody Against Human Urinary Tryspin Inhibitor by Single Radial Immunodiffusion: Use of Polyethylene glycol. J. of Immunological Methods. 80:117–123.*

Schmidt et al. 1996. Correlations for the partition behavior of proteins in aqueous two–phase systems: Effect of overall protein concentration. Biotech. and Bioeng. 50(6):617–626.*

Herbert et al. (eds.), "Dictionary of Immunology," 3rd edition, Blackwell Scientific Publications (1985).*

Leffell et al. (eds.), "Handbook of Human Immunology," CRC Press (1997).*

Tizard, "Immunology: An Introduction," Saunders College Publishing (1988).*

Toshihiko Takemura et al., "Acute phase reactant in urine: Urinary trypsin inhibitor in cases of children's infectious diseases", Japanese Journal of Inflammation, 1994, vol. 14, No. 1, pp. 53–57.

Susumu Maehara, "Study of Human Urinary Trypsin Inhibitor" I, II and III, Japanese Journal of Urology, 1983, vol. 74, No. 9, pp. 1627–1660.

Tadafumi Noda, 1992, Department of Laboratory Medicine, Osaka City University Medical School, 41:489–500, "Immunochemical Assay of Human Urinary Trypsin Inhibitor and its Clinical Meaning as an Acute–Phase Reactant".

Chemical Abstracts, 119:23263C "Automated measurement of urinary trypsin inhibitor an acute phase reactant in urine", S. Kuwajima.

Chemical Abstracts, 120:3942r "Utilization of polyspecific antiserum for specific radioimmunoassays; radioimmunoassays: for rat fetuin and bikunin were developed by using antiserum against total rat serum proteins", Edwin Fink.

Chemical Abstracts, 124:282328r "Identification of uronic–acid–rich protein as urinary bikunin, the light chain of inter–a –inhibitor", Fouad Atmani.

* cited by examiner

Primary Examiner—Lynette R. F. Smith
Assistant Examiner—Ja-Na Hines
(74) Attorney, Agent, or Firm—Merchant & Gould P.C.

(57) ABSTRACT

The present invention provides a method by which UTI concentration can be measured easily with high precision and good reproducibility. The measurement is performed by adding free anti-UTI antibodies to a sample and measuring the degree of the resulting agglutination, for example, from the change in absorbance. As shown in FIG. 3, the UTI concentration and the degree of the agglutination (i.e. the change in absorbance) are correlated. The absorbance can be measured by using a general spectrophotometer, preferably at a wavelength of 300 to 400 nm. Polyethylene glycol is preferably added to the reaction solution as an agglutination accelerator. The polyethylene glycol preferably has an average molecular weight of 2,000 to 20,000, and the concentration of polyethylene glycol in the reaction solution is preferably in the range of 2 to 10 weight %.

10 Claims, 2 Drawing Sheets

METHOD FOR MEASURING URINARY TRYPSIN INHIBITOR

FIELD OF THE INVENTION

The present invention relates to a method for measuring the concentration or the activity of urinary trypsin inhibitor (UTI) contained in body fluids. The presence of UTI was initially recognized in urine, but its presence has been confirmed in body fluids other than urine by subsequent studies. Therefore, the present invention can be applied to body fluids other than urine, for example, blood serum, blood plasma, cerebrospinal fluid, amniotic fluid, and other appropriate body fluids.

BACKGROUND OF THE INVENTION

UTI was discovered by Bauer and Reich in 1909 as a trypsin inhibitor which is present in urine. Since this, it has been reported that the amount of UTI present in urine significantly increases in patients with bacterial infections, malignant tumors (for example, gastric cancer, breast cancer, lung cancer), renal diseases or myocardial infarction, or patients having undergone surgical operations, pregnancy, or the like. Particularly in the field of pediatrics, its usefulness as an early indicator of bacterial infections has been noted (*Japanese Journal of Inflammation* 14: 53–57, 1994).

Conventionally, the activity or the concentration of UTI has been measured by enzymatic methods by measuring the inhibition of trypsin activity, or by various immunological methods based on the reaction between UTI and anti-UTI antibodies. Examples of immunological measuring methods include single radial immunodiffusion (SRID), radioimmunoassay (RIA), enzyme immunoassay (EIA), enzyme-linked immunosorbent assay (ELISA), latex agglutination immunoassay (LAIA), and the like.

In the above-mentioned enzymatic measuring methods, rapid measurement is enabled by the use of an automatic analyzer. However, because the inhibition of trypsin activity is measured, trypsin inhibitors other than UTI are also measured, so that there are problems in specificity. On the other hand, in the above-mentioned immunological measuring methods, because the measurement is based on antigen-antibody reaction, UTI alone can be measured specifically.

However, there are various problems in conventional immunological measuring methods. First, RIA has a problem in that the measurement can be carried out only in special facilities because of the use of radioactive materials. Furthermore, in SRID, EIA and ELISA, the operation of the measurement is complicated and also it requires a lot of time. On the other hand, in LAIA, measurement can be carried out easily within a short time, but if a normal automatic analyzer is used, the measured values may vary due to non-specific agglutination of latex, or the tubes and the like of the automatic analyzer may become clogged with dried reagents.

SUMMARY OF THE INVENTION

Thus, the usefulness of UTI as an indicator of various diseases has been recognized, but there are some problems in the measuring methods and so it has not been utilized sufficiently. Therefore, it is an object of the present invention to provide a method by which UTI can be measured rapidly and easily with high precision.

In order to achieve this object, the present invention provides a method for measuring the concentration of UTI in a sample, said method comprising preparing antibodies against UTI that are not adhered to an insoluble support (free anti-UTI antibodies), adding the antibodies to said sample, and measuring the degree of the resulting agglutination. Examples of the insoluble support include latex particles, gold colloid particles, and the like.

Thus, because the method of the present invention utilizes antigen-antibody reaction with excellent specificity, it is excellent in precision and reproducibility. Furthermore, because the degree of agglutination generated by the antigen-antibody reaction is measured, the measurement can be carried out easily without need of special operations such as immobilization of antibodies, or use of special equipment or apparatuses. Furthermore, compared with LAIA, it has an advantage of causing less contamination in an automatic analyzer.

The point of the present invention is that, with respect to UTI, it was found that agglutination reaction can be measured even if free anti-UTI antibodies that are not adhered to an insoluble support such as latex particles etc. are used. By not adhering antibodies to latex particles etc., the present invention has solved the problems of LAIA, and thus UTI can be measured speedily and easily with high precision.

In the method of the present invention, it is preferable to add antibodies into a sample in the presence of 2 to 10 weight % of polyethylene glycol in the reaction solution. The polyethylene glycol is used as an agglutination accelerator, which enables the measurement to be carried out more rapidly and accurately. By "the reaction solution" is understood an antigen-antibody reaction solution, namely, a solution containing a sample and free anti-UTI antibodies.

Preferably, the average molecular weight of the polyethylene glycol is in the range of 2,000 to 20,000.

In a particularly preferred embodiment, the average molecular weight and the concentration of the polyethylene glycol in the reaction solution are preferably in the range of 6,000 to 20,000 with respect to average molecular weight and 4 to 6 weight % with respect to concentration.

Any means of determining the degree of agglutination may be used. However, in the method of the present invention, the degree of the agglutination is preferably measured by an optical method. Although it is possible to measure the degree of the agglutination by visual observation, the measurement can be conducted more rapidly and accurately by optical measuring. In the optical measuring, for example, as mentioned below, the change in absorbance depending on the degree of agglutination is preferably measured. An alternative example of a measuring method other than optical measuring is an electrical resistance measuring method, in which the change in electrical resistance caused by the degree of agglutination is measured.

DETAILED DESCRIPTION OF THE INVENTION

Figure 1:
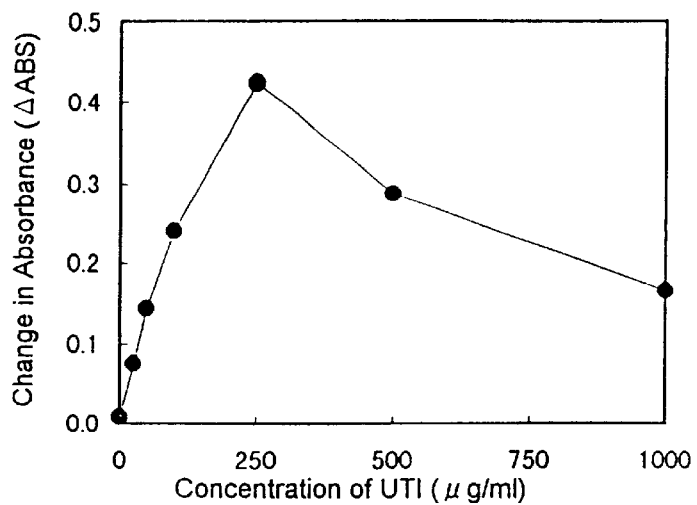
FIG. 1 is a graph showing the relationship between the UTI concentration and the change in absorbance.

The present invention will be further described in detail in the following.

In the present invention, free anti-UTI antibodies which react specifically with UTI are required, and furthermore, various other reagents for use in immunological measurements may be also used to enable the measurement to be performed under more suitable conditions. Examples of such reagents include buffer solutions, agglutination accelerators, stabilizers, antiseptics, and the like.

The free anti-UTI antibodies are not particularly limited as long as they react specifically with UTI and generate agglutination by antigen-antibody reaction. They may be any monoclonal or polydonal antibody, antiserum containing polyclonal antibodies, and the like. The type of antibody is also not limited, and any of immunoglobulin (Ig) A, IgE, IgG, IgM or IgD may be used. Furthermore, the origin of the antibodies is also not restricted, and they may be derived from rats, rabbits, goats, or any other appropriate source. The antibodies may be obtained by standard methods for producing antibodies (for example, by the method described in *Japanese Journal of Urology*, Vol. 74, No. 9, 1627–1640; 1983), except using UTI as the immunogen. Fragments of antibodies e.g. $Fab_2$ fragments or modified antibodies or antibody derivatives as are known on the art, e.g. single chain antibodies or chimaeric antibodies, might also be used as long as they retain the property of inducing agglutination. The term "antibody" as used herein encompasses all such fragments, modifications or derivatives. Furthermore, because the concentration of the free anti-UTI antibodies in the reaction solution affects the sensitivity and the upper limit of the measurement, it is preferable to determine a suitable amount of the free anti-UTI antibodies by experiments. Of course, the suitable amount should be determined in view of the titer and the degree of purification of the free anti-UTI antibodies.

The type of buffer solution used in the present invention is not particularly limited and e.g. may be any type commonly used in measurements utilizing antigen-antibody reactions. Examples include Tris buffer, Good's buffer, and the like. The pH of the buffer solution during the reaction is preferably in the range of 6 to 10.

In the present invention, it is preferable that the free anti-UTI antibodies are added to the sample in the presence of agglutination accelerators such as polyethylene glycol, polyvinyl alcohol, dextran, or the like, so that the sensitivity of the measurement may be enhanced. As mentioned above, polyethylene glycol is preferably used as the agglutination accelerator, and its average molecular weight is about 2,000 to 20,000, preferably about 6,000 or more. These various polyethylene glycols may be also used in combination.

The reaction solution of UTI and free anti-UTI antibodies may contain 2 to 10 weight % of polyethylene glycol, however, depending on the type of polyethylene glycol used, the concentration at which suitable sensitivity is obtained is varied. As the average molecular weight or the concentration of the polyethylene glycol increases, the agglutination accelerating action is enhanced. However, if the concentration of the polyethylene glycol in the reaction solution is as high as about 10 weight % or more, non-specific agglutination reactions increase, so that errors may occur in the measurement. Accordingly, it is preferable to use 4 to 6 weight % of polyethylene glycol having an average molecular weight of about 6,000 to 20,000 in the reaction solution.

Furthermore, although not limited to polyethylene glycol, if an agglutination accelerator is used at a high concentration, the possibility of occurrence of non-specific agglutination reactions, other than antigen-antibody reactions, increases as mentioned above. Therefore, if it affects the precision of the measurement, preventative measures, for example, adding inorganic salts such as sodium chloride or nonionic surfactants, may be necessary.

Examples of the stabilizer include sugars, proteins, surfactants, and the like, and those normally used in this field may be used at any proper concentration depending on their effects.

The sample to be measured in the present invention is usually, but need not be limited to, urine. That is, although the presence of UTI was initially recognized in urine, subsequent studies have confirmed the presence of UTI in body fluids other than urine. Therefore, the present invention can be also applied to body fluids other than urine, for example, serum, plasma (or any blood-derived sample), cerebrospinal fluid, amniotic fluid, or any other appropriate body fluid.

In the measurement of the present invention, the degree of agglutination is preferably determined by measuring the change in absorbance. The wavelength used in this measurement is usually 300 to 400 nm. Furthermore, the measuring apparatus used is usually a spectrophotometer, but it is preferably an automatic analyzer comprising a spectrophotometer.

Next, the present invention will now be further described by the following nor limiting Examples.

EXAMPLE 1

Measurement of the UTI Concentration

As shown below, the relationship between the concentration of UTI and the change in absorbance was examined. The analyzer used in the measurement was an automatic analyzing apparatus (type 7070, produced by Hitachi, Ltd.).

Sample for Measurement

Purified UTI (UTININE, produced by MECT) was dissolved in 0.9 weight % physiological sodium chloride solution to prepare UTI solutions having various concentrations of 0 μg/ml, 2.5 μg/ml, 5 μg/ml, 10 μg/ml, 15 μg/ml, 25 μg/ml, 50 μg/ml, 100 μg/ml, 250 μg/ml, 500 μg/ml and 1,000 μg/ml, respectively, and the change in absorbance of each solution was measured by the following method.

Reagent for Measurement

A. Buffer Solution (First Reagent Solution)

6 weight % of polyethylene glycol (#6000, produced by Nacalai tesque) and 0.05 weight % of Triton-X100 (produced by Nacalai tesque) were dissolved in 100 mM Tris-HCl buffer solution (pH 7.4) containing 0.1 weight % of sodium azide to prepare the first reagent solution.

B. Antibody Solution (Second Reagent Solution)

Free anti-UTI antibodies were dissolved at a ratio of 2.5 mg/ml in 100 mM Tris-HCl buffer solution (pH 7.4) containing 0.3 weight % of sodium azide to prepare the second reagent solution. The amount of the protein was determined from the absorbance at 280 nm, using human IgG as the standard substance. Furthermore, the free anti-UTI antibodies were prepared by the following method.

Method for Preparing Free Anti-UTI Antibodies

Antiserum was obtained by immunizing a rabbit (Japanese white, female) against purified UTI five times at two-week intervals. The first immunization was performed by an intracutaneous injection of 0.25 mg of UTI with a complete Freund's adjuvant, and the second to fifth immunizations were performed by an intracutaneous injection of 0.5 mg of purified UTI with an incomplete Freund's adjuvant at each. Then, blood was taken from the rabbit ten days after the fifth immunization, and the obtained antiserum was purified by protein A affinity chromatography and the concentration of the purified product was adjusted to an appropriate level with 100 mM Tris-HCl buffer solution (pH 7.4) containing 0.3 weight % of sodium azide so as to prepare an anti-UTI antibody solution.

Procedures for Measurement

First, 230 μl of the first reagent solution was mixed with 10 μl of the sample for measurement, and the mixture was incubated at 37° C. for five minutes. Absorbance at a wavelength of 340 nm (ABS1) was measured. 60 μl of the second reagent solution was pipetted into the reaction solution, and after allowing it to react at 37° C. for five minutes, absorbance at a wavelength of 340 nm (ABS2) was measured. After compensating for the change in the liquid volume, the change in absorbance (ΔABS) was determined from the ABS1 and ABS2 by the equation below (Formula 1). The results are shown in Table 1 below and in the graph of FIG. 1.

$$\Delta ABS = ABS2 - ABS1 \times (240/300)$$
[Formula 1]

TABLE 1

| UTI concentration (μg/ml) | 0.0 | 2.5 | 5.0 | 7.5 | 10.0 | 15.0 | 25.0 |
|---|---|---|---|---|---|---|---|
| ΔABS | 0.0085 | 0.0130 | 0.0181 | 0.0231 | 0.0349 | 0.0433 | 0.0752 |

As shown in FIG. 1, with respect to the UTI concentrations exceeding 250 μg/ml, the ΔABS decreased because of prozone caused by excess antigens, but the ΔABS increased depending on the concentration up to 250 μg/ml. The expression "prozone" as used herein means a phenomena that crosslinking reaction of antibodies does not occur and agglutination lump does not form if too many antibodies exist. Furthermore, as is understood from the results in Table 1, UTI can be detected at least in the range of concentration not less than 2.5 μg/ml.

EXAMPLE 2

Measurement of Urine Sample

A calibration curve was obtained by measuring the change in absorbance in aqueous UTI solutions (concentrations: 0 μg/ml, 25 μg/ml, 50 μg/ml and 100 μg/ml, respectively) in the same way as in Example 1. From this calibration curve, the ΔABS in three samples of urine obtained from healthy adults (measured ten times simultaneously for each as in Example 1) were converted into concentrations so as to be within-run precision (to confirm reproducibility). The results are shown in Table 2 below. In Table 2, SD denotes standard deviation, and CV denotes coefficient of variation.

TABLE 2

|  | Urine A | Urine B | Urine C |
|---|---|---|---|
| (Concentration Measured: μg/ml) | 13.3 | 49.6 | 2.7 |
|  | 13.4 | 49.6 | 2.6 |
|  | 13.5 | 49.5 | 2.8 |
|  | 13.4 | 49.7 | 2.7 |
|  | 13.4 | 49.6 | 2.6 |
|  | 13.2 | 49.7 | 2.6 |
|  | 13.1 | 49.4 | 2.5 |

TABLE 2-continued

|  | Urine A | Urine B | Urine C |
|---|---|---|---|
|  | 13.6 | 50.2 | 2.6 |
|  | 13.1 | 49.5 | 2.4 |
|  | 13.5 | 50.1 | 2.6 |
| Average value (μg/ml) | 13.4 | 49.7 | 2.6 |
| SD value (μg/ml) | 0.2 | 0.3 | 0.1 |
| CV value (%) | 1.3 | 0.5 | 4.2 |

As shown in Table 2 above, the three samples, including one having a concentration of as low as 2.6 μg/ml, were able to be measured with good reproducibility.

EXAMPLE 3

Test of Adding UTI to Urine

Figure 2:
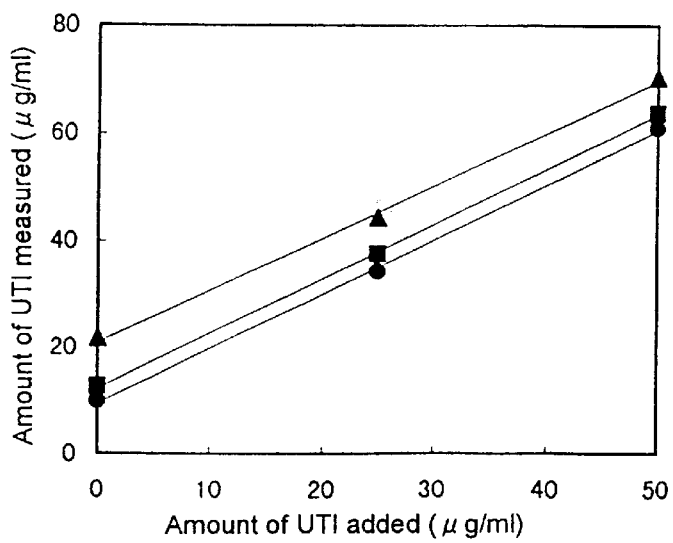
FIG. 2 is a graph showing the relationship between the amount of UTI added to urine and the change in absorbance.

Into each of three urine samples (D, E, F), either 25 μg or 50 μg of purified UTI was added. Each mixture was measured by the same method as in Example 2 to determine the UTI concentration. The results of the measurement are shown in the graph of FIG. 2. In FIG. 2, -▲- shows the urine sample D, -■- shows the urine sample E, and -●- shows the urine sample F, respectively.

As shown in the graph of FIG. 2, the measured values increase in proportion to the amount of UTI added, so that it is understood that the amounts of purified UTI added were accurately measured.

EXAMPLE 4

Figure 3:
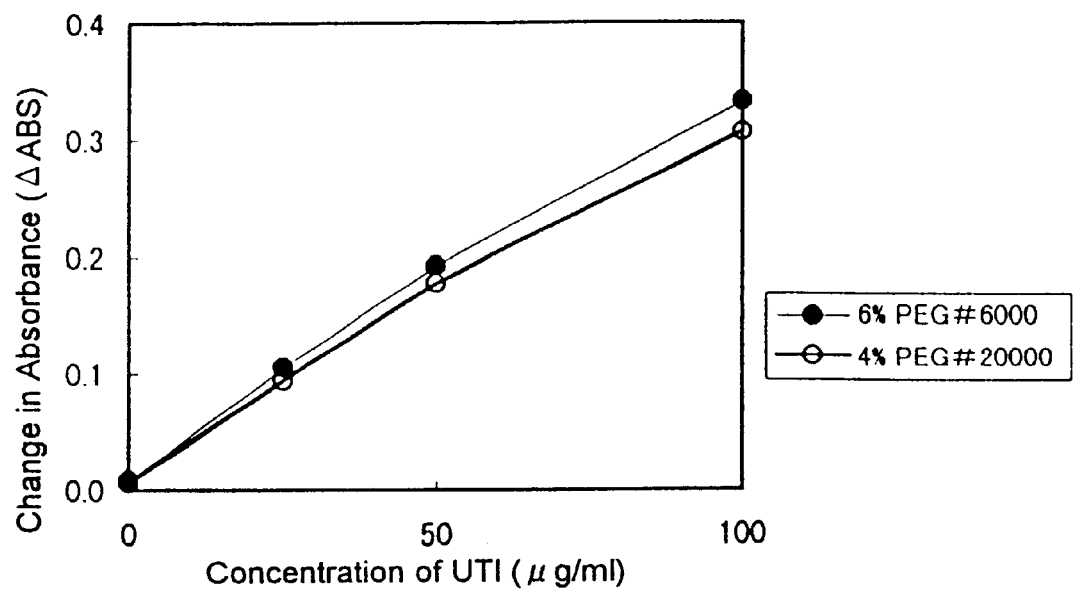
FIG. 3 is a graph showing the relationship between the UTI concentration and the change in absorbance when the average molecular weight and the concentration of polyethylene glycol are varied.

Consideration of the Concentration and the Average Molecular Weight of the Polyethylene Glycol The concentration of UTI was measured by the same method as in Example 1 except in that 4 weight % of polyethylene glycol having an average molecular weight of 20,000 (#20,000, produced by Nacalai tesque) was contained in the reaction solution. However, only UTI solutions containing purified UTI at a rate of 0 μg/ml, 25 μg/ml, 50 μg/ml and 100 μg/ml, were prepared. The results of the measurement are shown in the graph of FIG. 3. This graph also shows an example in which the same measurement as in Example 1 was performed except in that 6 weight % of polyethylene glycol having an average molecular weight of 6,000 (#6,000, produced by Nacalai tesque) was contained in the reaction solution.

From the graph in FIG. 3, it is understood that if polyethylene glycol having an average molecular weight of 20,000 is used, the same level of sensitivity can be obtained even at a lower concentration than in the case of the polyethylene glycol having an average molecular weight of 6,000.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method for measuring in solution the concentration of urinary trypsin inhibitor in a sample comprising:

adding antibodies against urinary trypsin inhibitor that are not adhered to an insoluble support to the sample in a reaction solution;

measuring the degree of the resulting agglutination or precipitation in the reaction solution; and correlating the degree of agglutination or precipitation to the inhibitor concentration.

2. The method according to claim 1, in which the antibodies are added to the sample in the presence of 2 to 10 weight % of polyethylene glycol in the reaction solution.

3. The method according to claim 1, in which the antibodies are added to the sample in the presence of polyethylene glycol having an average molecular weight of 2,000 to 20,000.

4. The method according to claim 1, in which the antibodies are added to the sample in the presence of 4 to 6 weight % of polyethylene glycol having an average molecular weight of 6,000 to 20,000 in the reaction solution.

5. The method according to claim 1, in which the degree of the agglutination or precipitation is measured by an optical method.

6. The method according to claim 1, in which the sample is at least one body fluid selected from the group consisting of urine, serum, plasma, cerebrospinal fluid and amniotic fluid.

7. The method according to claim 1, in which further reagents which enhance the immunological reaction or measurement thereof are incorporated, said reagents being buffer solutions, agglutination accelerators, stabilizer or antiseptics.

8. The method according to claim 7, in which said agglutination accelerators are polyethylene glycol, polyvinyl alcohol or dexter.

9. The method according to claim 7, in which said stabilizers are sugars, proteins or surfactants.

10. The method according to claim 1, in which non-specific agglutination reactions are prevented by the further incorporation of inorganic salts or non-ionic surfactants.

* * * * *